United States Patent
Fischer et al.

(10) Patent No.: US 9,668,833 B2
(45) Date of Patent: Jun. 6, 2017

(54) ABUTMENT AND METHOD OF ATTACHING AN ABUTMENT TO A DENTAL IMPLANT

(71) Applicant: Nobel Biocare Services AG, Kloten (CH)

(72) Inventors: Thomas Fischer, Rapperswil (CH); Henrik Peterson, Zürich (CH); David Sollberger, Zürich (CH); Thomas Eriksson, Gothenburg (SE); Lars Jorneus, Frillesås (SE); Adrian Haus, Zürich (SE); Mikael Brunell, Mariefred (SE)

(73) Assignee: Nobel Biocare Services AG, Kloten (CH)

( * ) Notice: Subject to any disclaimer, the term of this patent is extended or adjusted under 35 U.S.C. 154(b) by 53 days.

(21) Appl. No.: 14/654,407

(22) PCT Filed: Dec. 17, 2013

(86) PCT No.: PCT/EP2013/003807
§ 371 (c)(1),
(2) Date: Jun. 19, 2015

(87) PCT Pub. No.: WO2014/095034
PCT Pub. Date: Jun. 26, 2014

(65) Prior Publication Data
US 2015/0305836 A1 Oct. 29, 2015

(30) Foreign Application Priority Data
Dec. 21, 2012 (GB) .............................. GB1223202.1

(51) Int. Cl.
A61C 8/00 (2006.01)

(52) U.S. Cl.
CPC ............ *A61C 8/0062* (2013.01); *A61C 8/006* (2013.01); *A61C 8/0012* (2013.01);
(Continued)

(58) Field of Classification Search
CPC combination set(s) only.
See application file for complete search history.

(56) References Cited

U.S. PATENT DOCUMENTS 2,721,387 A 10/1955 Ashuckian
4,259,072 A 3/1981 Hirabayashi et al.
(Continued)

FOREIGN PATENT DOCUMENTS

AU A-75458/96 6/1997
CH 692 542 7/2002
(Continued)

OTHER PUBLICATIONS

Brodbeck, Urs, "The ZiReal Post: A New Ceramic Implant Abutment," J Esthet Restor Dent 15:10-24, 2003.
(Continued)

*Primary Examiner* — Jan Christopher Merene
(74) *Attorney, Agent, or Firm* — Knobbe, Martens, Olson & Bear LLP (57) ABSTRACT

The present invention relates to an abutment (10, 100), comprising: a ceramic part (12, 112); and a metal adapter (14, 114) removably attachable to the ceramic part, wherein the metal adapter has a conical connection interface (16) for attachment to a dental implant (18). The present invention also relates to a method of attaching an abutment (10) to a dental implant (18).

14 Claims, 9 Drawing Sheets

(52) U.S. Cl.
CPC .......... *A61C 8/0054* (2013.01); *A61C 8/0068* (2013.01); *A61C 8/0069* (2013.01); *F04C 2270/0421* (2013.01)

(56) References Cited

U.S. PATENT DOCUMENTS

| | | | |
|---|---|---|---|
| 4,560,353 A | 12/1985 | Schulte et al. | |
| 4,575,340 A | 3/1986 | Lustig | |
| 4,746,293 A | 5/1988 | Lundgren et al. | |
| 4,758,161 A | 7/1988 | Niznick | |
| 4,763,788 A | 8/1988 | Jörnéus et al. | |
| 4,824,372 A | 4/1989 | Jörnéus et al. | |
| 4,846,683 A | 7/1989 | Lazzara et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |
| 4,872,839 A | 10/1989 | Brajnovic | |
| 4,904,187 A | 2/1990 | Zingheim | |
| 4,955,811 A | 9/1990 | Lazzara et al. | |
| 4,988,297 A | 1/1991 | Lazzara et al. | |
| 4,988,298 A | 1/1991 | Lazzara et al. | |
| 5,000,686 A | 3/1991 | Lazzara et al. | |
| 5,006,069 A | 4/1991 | Lazzara et al. | |
| 5,015,186 A | 5/1991 | Detsch | |
| 5,022,860 A | 6/1991 | Lazzara et al. | |
| 5,030,096 A | 7/1991 | Hurson et al. | |
| 5,035,619 A | 7/1991 | Daftary | |
| 5,040,982 A | 8/1991 | Stefan-Dogar | |
| 5,040,983 A | 8/1991 | Binon | |
| 5,064,373 A | 11/1991 | Staubli et al. | |
| 5,064,375 A | 11/1991 | Jörnéus | |
| 5,069,622 A | 12/1991 | Rangert et al. | |
| 5,071,345 A | 12/1991 | Rosen | |
| 5,071,351 A | 12/1991 | Green, Jr. et al. | |
| 5,073,111 A | 12/1991 | Daftary | |
| 5,082,442 A | 1/1992 | Rosen | |
| 5,087,200 A | 2/1992 | Brajnovic et al. | |
| 5,100,323 A | 3/1992 | Friedman et al. | |
| 5,105,690 A | 4/1992 | Lazzara et al. | |
| 5,106,300 A | 4/1992 | Voitik | |
| 5,125,839 A | 6/1992 | Ingber et al. | |
| 5,125,841 A | 6/1992 | Carlsson et al. | |
| 5,135,395 A | 8/1992 | Marlin | |
| 5,145,371 A | 9/1992 | Jörnéus | |
| 5,145,372 A | 9/1992 | Daftary et al. | |
| 5,152,687 A | 10/1992 | Amino | |
| 5,154,612 A | 10/1992 | Carlsson et al. | |
| 5,169,309 A | 12/1992 | Staubli et al. | |
| 5,188,800 A | 2/1993 | Green, Jr. et al. | |
| 5,209,659 A | 5/1993 | Friedman et al. | |
| 5,209,666 A | 5/1993 | Balfour et al. | |
| 5,213,502 A | 5/1993 | Daftary | |
| 5,238,405 A | 8/1993 | Marlin | |
| 5,246,370 A | 9/1993 | Coatoam | |
| 5,259,759 A | 11/1993 | Jörnéus et al. | |
| 5,269,685 A | 12/1993 | Jörnéus et al. | |
| 5,281,140 A | 1/1994 | Niznick | |
| 5,282,746 A | 2/1994 | Sellers et al. | |
| 5,292,252 A | 3/1994 | Nickerson et al. | |
| 5,297,963 A | 3/1994 | Daftary | |
| 5,316,476 A | 5/1994 | Krauser | |
| 5,334,024 A | 8/1994 | Niznick | |
| 5,336,090 A | 8/1994 | Wilson, Jr. et al. | |
| 5,338,196 A | 8/1994 | Beaty et al. | |
| 5,344,457 A | 9/1994 | Pilliar et al. | |
| 5,350,302 A | 9/1994 | Marlin | |
| 5,368,483 A | 11/1994 | Sutter et al. | |
| 5,417,568 A | 5/1995 | Giglio | |
| 5,419,702 A | 5/1995 | Beaty et al. | |
| 5,431,567 A | 7/1995 | Daftary | |
| 5,439,380 A | 8/1995 | Marlin | |
| 5,447,435 A | 9/1995 | Brodbeck | |
| 5,476,383 A | 12/1995 | Beaty et al. | |
| 5,492,471 A | 2/1996 | Singer | |
| 5,564,921 A | 10/1996 | Marlin | |
| 5,584,694 A | 12/1996 | Forsmalm et al. | |
| 5,658,147 A | 8/1997 | Phimmasone | |
| 5,662,474 A | 9/1997 | Jörnéus et al. | |
| 5,685,714 A | 11/1997 | Beaty et al. | |
| 5,702,252 A | 12/1997 | Rogers et al. | |
| 5,725,375 A | 3/1998 | Rogers | |
| 5,741,267 A | 4/1998 | Jörnéus et al. | |
| 5,829,977 A | 11/1998 | Rogers et al. | |
| 5,873,720 A | 2/1999 | Jörnéus et al. | |
| 5,873,722 A | 2/1999 | Lazzara et al. | |
| RE36,126 E | 3/1999 | Beaty et al. | |
| 5,904,483 A | 5/1999 | Wade | |
| 5,934,906 A | 8/1999 | Phimmasone | |
| 5,947,732 A | 9/1999 | Beaty et al. | |
| 5,989,026 A | 11/1999 | Rogers et al. | |
| 6,012,923 A | 1/2000 | Bassett et al. | |
| 6,048,203 A | 4/2000 | Rosenberg | |
| RE36,689 E | 5/2000 | Beaty et al. | |
| 6,068,479 A | 5/2000 | Kwan | |
| 6,152,737 A | 11/2000 | Beaty et al. | |
| 6,159,008 A | 12/2000 | Kumar | |
| 6,168,435 B1 | 1/2001 | Beaty et al. | |
| 6,174,166 B1 | 1/2001 | Jörnéus | |
| 6,196,842 B1 | 3/2001 | Jörnéus | |
| 6,227,856 B1 | 5/2001 | Beaty et al. | |
| RE37,227 E | 6/2001 | Brodbeck | |
| 6,276,938 B1 | 8/2001 | Jörnéus et al. | |
| 6,290,499 B1 | 9/2001 | Lazzara et al. | |
| 6,343,930 B1 | 2/2002 | Beaty et al. | |
| 6,358,050 B1 | 3/2002 | Bergstrom et al. | |
| 6,382,977 B1 | 5/2002 | Kumar | |
| 6,394,806 B1 | 5/2002 | Kumar | |
| 6,394,809 B2 | 5/2002 | Rogers et al. | |
| 6,419,489 B1 | 7/2002 | Jörnéus et al. | |
| 6,561,805 B2 | 5/2003 | Kumar | |
| 6,626,911 B1 | 9/2003 | Engman et al. | |
| 6,644,969 B2 | 11/2003 | Kumar | |
| 6,655,962 B1 | 12/2003 | Kennard | |
| 6,733,291 B1 | 5/2004 | Hurson | |
| 6,769,913 B2 | 8/2004 | Hurson | |
| 6,827,575 B1 | 12/2004 | Jörnéus | |
| 6,848,908 B2 | 2/2005 | Björn et al. | |
| 6,896,517 B1 | 5/2005 | Björn et al. | |
| 6,902,401 B2 | 6/2005 | Jörnéus et al. | |
| 7,008,228 B2 | 3/2006 | Björn et al. | |
| 7,108,510 B2 | 9/2006 | Niznick | |
| 7,338,286 B2 | 3/2008 | Porter et al. | |
| 7,363,239 B1 | 4/2008 | Andersson et al. | |
| 7,484,959 B2 | 2/2009 | Porter et al. | |
| 7,491,058 B2 | 2/2009 | Jörnéus et al. | |
| 7,665,989 B2 | 2/2010 | Brajnovic et al. | |
| 8,033,826 B2 | 10/2011 | Towse | |
| 8,038,445 B2 | 10/2011 | Brajnovic et al. | |
| 8,231,825 B2 | 7/2012 | Eriksson et al. | |
| 8,272,871 B2 | 9/2012 | Hurson | |
| 8,608,473 B2 | 12/2013 | Kennard | |
| 8,747,112 B2 * | 6/2014 | Brun | A61C 8/0001 433/173 |
| 8,805,658 B2 | 8/2014 | Pettersson et al. | |
| 8,915,735 B1 | 12/2014 | Carlsson et al. | |
| 9,125,708 B2 | 9/2015 | Carvalho et al. | |
| 2002/0192620 A1 | 12/2002 | Jörnéus et al. | |
| 2003/0104336 A1 | 6/2003 | Sethi et al. | |
| 2003/0124488 A1 | 7/2003 | Gittleman | |
| 2003/0162149 A1 | 8/2003 | Björn et al. | |
| 2004/0038179 A1 | 2/2004 | Kumar | |
| 2005/0019731 A1 | 1/2005 | Björn et al. | |
| 2005/0065525 A1 | 3/2005 | Aringskog et al. | |
| 2006/0008772 A1 | 1/2006 | Brajnovic et al. | |
| 2006/0110706 A1 | 5/2006 | Jörnéus et al. | |
| 2006/0246396 A1 | 11/2006 | Suttin et al. | |
| 2007/0117066 A1 | 5/2007 | Jörnéus et al. | |
| 2007/0281278 A1 | 12/2007 | Jörnéus et al. | |
| 2008/0102420 A1 | 5/2008 | Porter et al. | |
| 2008/0166682 A1 | 7/2008 | Björn et al. | |
| 2008/0261175 A1 * | 10/2008 | Hurson | A61C 8/0025 433/173 |
| 2009/0081612 A1 | 3/2009 | Jörnéus et al. | |

(56) References Cited

U.S. PATENT DOCUMENTS

| | | |
|---|---|---|
| 2009/0130629 A1 | 5/2009 | Towse et al. |
| 2009/0136899 A1 | 5/2009 | Porter et al. |
| 2009/0239200 A1 | 9/2009 | Brajnovic et al. |
| 2009/0298013 A1 | 12/2009 | Baruc |
| 2010/0291509 A1 | 11/2010 | Berggren et al. |
| 2010/0297583 A1 | 11/2010 | Benzon et al. |
| 2010/0311011 A1 | 12/2010 | Schwieder et al. |
| 2010/0323327 A1 | 12/2010 | Eriksson et al. |
| 2011/0014586 A1 | 1/2011 | Jörnéus et al. |
| 2011/0060558 A1 | 3/2011 | Pettersson et al. |
| 2011/0123948 A1 | 5/2011 | Hinrichsen |
| 2011/0123953 A1 | 5/2011 | Jörnéus et al. |
| 2011/0183291 A1 | 7/2011 | Malo Carvalho et al. |
| 2012/0009545 A1 | 1/2012 | Eriksson et al. |
| 2012/0077150 A1 | 3/2012 | Goodman et al. |
| 2012/0191097 A1 | 7/2012 | Jörnéus et al. |
| 2012/0191103 A1 | 7/2012 | Jörnéus et al. |
| 2012/0295224 A1 | 11/2012 | Jörnéus et al. |
| 2012/0301850 A1 | 11/2012 | Sollberger et al. |
| 2012/0326343 A1 | 12/2012 | Eriksson et al. |
| 2013/0017513 A1 | 1/2013 | Lutz et al. |
| 2013/0045463 A1 | 2/2013 | Lindstrom et al. |
| 2014/0011160 A1 | 1/2014 | Jörnéus et al. |
| 2014/0124374 A1 | 5/2014 | Eriksson et al. |
| 2014/0178836 A1 | 6/2014 | Haus et al. |
| 2014/0186797 A1 | 7/2014 | Haus |
| 2015/0230890 A1 | 8/2015 | Malo Carvalho et al. |
| 2015/0342708 A1 | 12/2015 | Haus |

FOREIGN PATENT DOCUMENTS

| | | |
|---|---|---|
| DE | 27 17 506 | 5/1978 |
| DE | 32 24 112 | 2/1984 |
| DE | 34 44 780 | 6/1986 |
| DE | 38 25 601 | 3/1989 |
| DE | 41 27 839 | 3/1992 |
| DE | 42 30 009 | 1/1993 |
| DE | 101 29 684 A1 | 1/2003 |
| DE | 10 2009 05775 A1 | 6/2011 |
| EP | 0 377 068 B1 | 11/1992 |
| EP | 0 534 078 A1 | 3/1993 |
| EP | 0 320 024 B1 | 12/1993 |
| EP | 0 474 571 B1 | 4/1995 |
| EP | 0 477 644 B1 | 5/1996 |
| EP | 0 657 146 B1 | 4/1998 |
| EP | 1 269 932 A1 | 1/2003 |
| EP | 1 073 381 B1 | 9/2004 |
| EP | 0 786 966 B1 | 5/2006 |
| EP | 0 837 658 B1 | 4/2007 |
| EP | 1 021 997 B1 | 5/2007 |
| EP | 1 124 501 B1 | 6/2007 |
| EP | 2 025 302 A1 | 2/2009 |
| EP | 2 090 263 A1 | 8/2009 |
| EP | 2 127 612 A1 | 12/2009 |
| EP | 1 613 237 B1 | 2/2011 |
| EP | 1 419 746 B1 | 6/2011 |
| EP | 1 820 467 B1 | 7/2015 |
| GB | 1 305 478 | 1/1973 |
| GB | 2 213 065 | 8/1989 |
| GB | 2 487 553 | 8/2012 |
| WO | WO 93/02632 | 2/1993 |
| WO | WO 97/10770 | 3/1997 |
| WO | WO 00/24335 | 5/2000 |
| WO | WO 03/049636 | 6/2003 |
| WO | WO 2004/002358 | 1/2004 |
| WO | WO 2008/128757 | 10/2008 |
| WO | WO 2014/095033 | 6/2014 |

OTHER PUBLICATIONS

International Search Report for Application No. PCT/EP2013/003806 mailed on Mar. 19, 2014 in 4 pages. [the ISR for the PCT Application of U.S. Appl. No. 14/654,440].

International Search Report for Application No. PCT/EP2013/003807 mailed on Apr. 9, 2014 in 5 pages. [the ISR for the PCT Application of this US national phase application].

* cited by examiner

ABUTMENT AND METHOD OF ATTACHING AN ABUTMENT TO A DENTAL IMPLANT

CROSS-REFERENCE TO RELATED APPLICATIONS

This application is a national stage application under 35 U.S.C. §371 of International Application No. PCT/EP2013/003807, filed on Dec. 17, 2013, which published in English as WO 2014/095034 A1 on Jun. 26, 2014 and which claims priority benefit of GB Patent Application No. 1223202.1 filed on Dec. 21, 2012.

The present invention relates an abutment. The present invention also relates to a method of attaching an abutment to a dental implant.

The prior art includes zirconia abutments for internal conical connection dental implants. It may be desired to have the complete abutment in zirconia for aesthetic purposes. However, it may also be desirable to further improve the strength of such an abutment.

The present invention is defined in the appended independent claims. Embodiments are defined in the appended dependent claims.

According to an aspect of the present invention, there is provided an abutment comprising: a ceramic part; and a metal adapter removably attachable to the ceramic part, wherein the metal adapter has a conical connection interface for attachment to a dental implant.

By providing a non-brittle metal adapter which has the conical connection interface towards the dental implant, the strength of the abutment may be improved. Still high esthetics are maintained due to the ceramic part. Also, since the metal adapter is removably attachable to the ceramic part, it can conveniently be removed from the ceramic part e.g. when porcelain is fused to the ceramic part so that the metal adapter is not heated. It should be noted that metal adapters/portions are known per se from WO2004002358 and U.S. Pat. No. 6,168,435 and US2012077150, but not for conical connection. Also, the metal adapter in WO2004002358 is not load-bearing—it only prevents rotation. Also, the metal portions in U.S. Pat. No. 6,168,435 and US2012077150 appear not to be removably attachable to the ceramic part.

The metal adapter may comprise at least one flexible arm with a protrusion adapted to press against a side wall and/or snap into a corresponding recess (if there is any) of the ceramic part for securing the metal adapter to the ceramic part in the coronal-apical direction, wherein the metal adapter comprises at least one convex surface adapted to abut against at least one corresponding concave surface of the ceramic part for preventing rotation between the ceramic part and the metal adapter.

The metal adapter may at its coronal end have a central protruding portion which is adapted to be received in a central apical recess of the ceramic part, wherein said central protruding portion may accommodate said at least one flexible arm (with the protrusion) and said at least one convex surface.

Said at least one convex surface may be three convex surfaces uniformly distributed in the circumferential direction on the metal adapter, wherein said at least one corresponding concave surface is three concave surfaces uniformly distributed in the circumferential direction in ceramic part, and wherein the metal adapter comprises three flexible arms and protrusions arranged between the three convex surfaces.

The metal adapter may include a load-bearing circumferential surface adapted to abut against a corresponding circumferential surface of the ceramic part.

The conical connection interface of the metal adapter may include an external conical shape tapering towards the apical end of the metal adapter and adapted to mate with a corresponding conical surface of the dental implant, and an external indexed portion provided apically of the conical shape adjacent to the apical end of the metal adapter.

The metal adapter may include an outer surface devised for soft tissue apposition.

Said outer surface may be arranged between said load-bearing circumferential surface and said external conical shape.

The ceramic part may comprise a screw channel passing through the ceramic part and forming a first opening at a first end and a second opening at an apical end, and a screw seat proximal to the apical end of the screw channel for seating the head of a screw for the fixation of the abutment to the dental implant.

In one or more embodiments, the longitudinal axis of the screw channel at the first end does not match the longitudinal axis of the screw channel at the apical end.

The metal adapter may comprise a bore passing through the metal adapter and forming a coronal opening and an apical opening, wherein the bore is provided with an internal thread.

The ceramic part may be adapted to support a dental restoration.

The ceramic part may be a full-contour part.

According to another aspect of the present invention, the abutment is provided in combination with the dental implant.

According to yet another aspect of the present invention, there is provided a method of attaching the abutment with an outer surface devised for soft tissue apposition to a dental implant anchored in a jaw bone of a patient, wherein the coronal end of the dental implant is substantially in level with the surface or crest of the jaw bone, which method comprises: attaching the abutment to the dental implant, such that said outer surface of the metal adapter is exposed to soft tissue or gum overlying the jaw bone. This aspect may exhibit the same or similar features and/or technical effects as the previously discussed aspects, and vice versa These and other aspects of the present invention will now be described in more detail, with reference to the appended drawings showing currently preferred embodiments of the invention.

FIG. 1b is a cross-sectional view of the abutment in FIG. 1a.

FIG. 2b is a cross-sectional view of the metal adapter in FIG. 2a.

FIG. 3a is a perspective view of the ceramic part of FIGS. 1a-1b.

FIG. 3b is a cross-sectional view of the ceramic part in FIG. 3a.

FIG. 4b is a cross-sectional view of the arrangement in FIG. 4a.

Figure 1A:
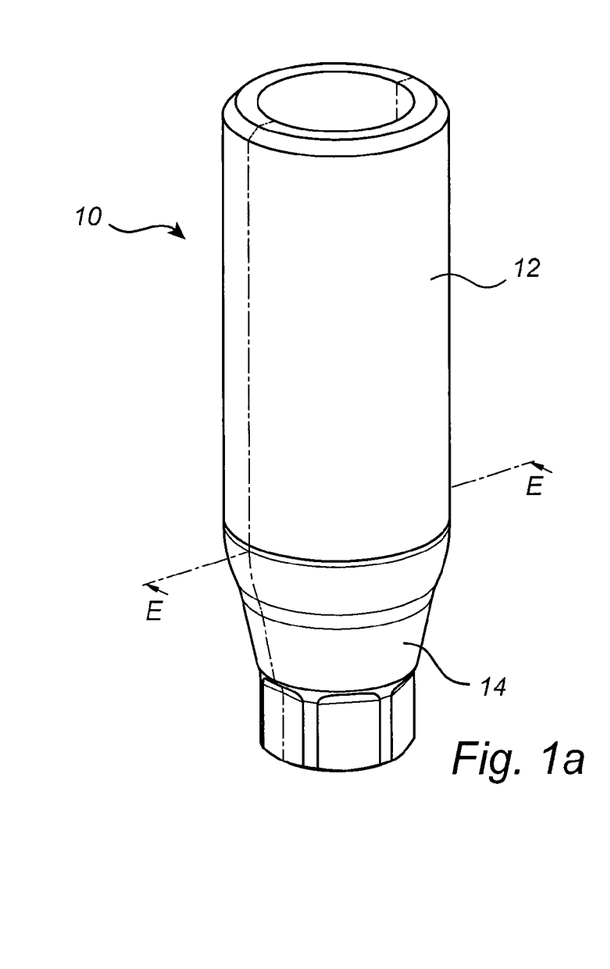
FIG. 1a is a perspective view of an abutment with a ceramic part and a metal adapter according to an embodiment of the present invention.
Figure 1B:
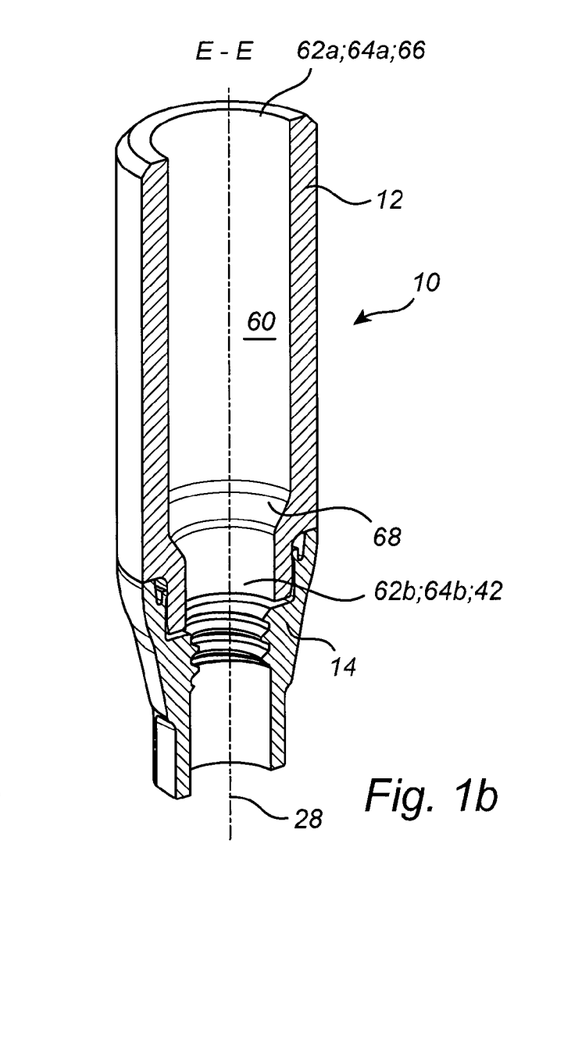

FIGS. 1a-1b show an abutment 10 according to an embodiment of the present invention.

The abutment 10 comprises a coronal ceramic part 12. The ceramic part 12 may be adapted to support a dental restoration or a dental prosthesis, such as a single-unit restoration (crown) or a bridge. The restoration or prosthesis may for example be cemented to the ceramic part 12. Alternatively, the ceramic part of the present abutment may be a full-contour part. The ceramic part 12 is preferably made entirely of ceramic material such as zirconia.

Figure 2A:
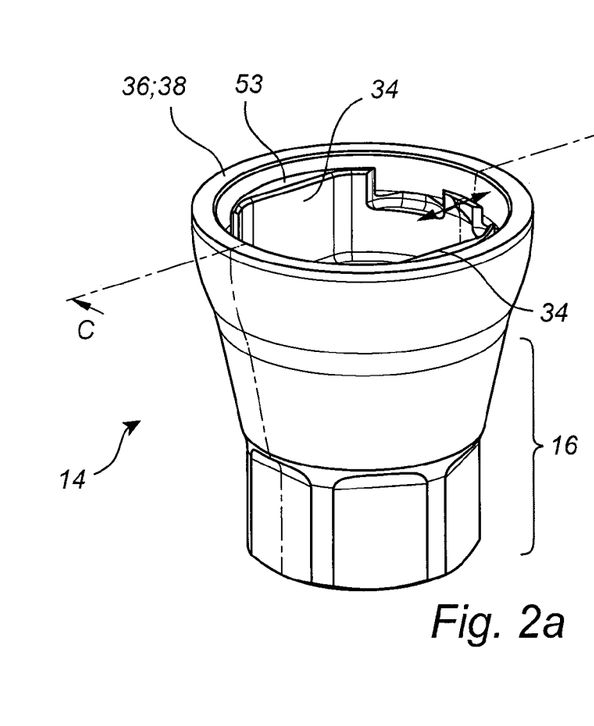
FIG. 2a is a perspective view of the metal adapter of FIGS. 1a-1b.
Figure 2B:
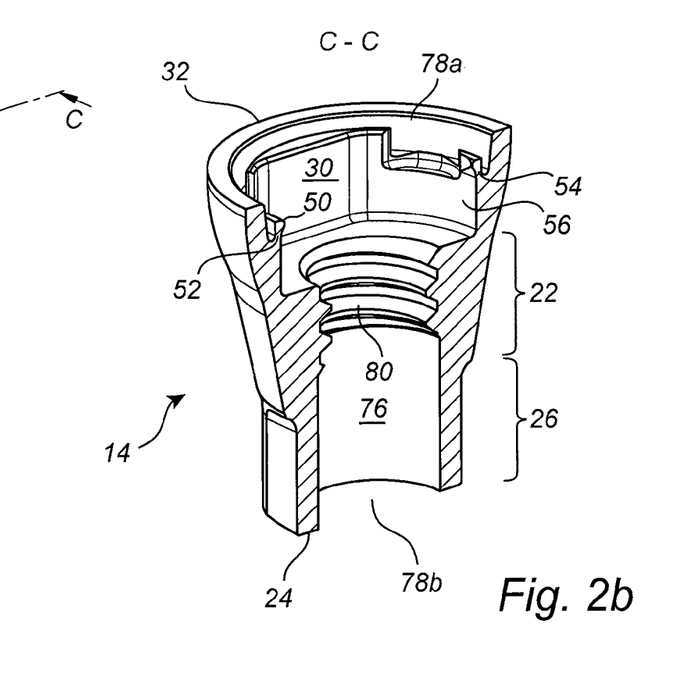

The abutment 10 further comprises an apical metal adapter 14. The metal adapter 14 is also shown in FIGS. 2a-2b. The metal adapter 14 is for example made of titanium or titanium alloy. The metal adapter 14 has a conical connection interface generally designated with reference sign 16 (FIG. 2a). The conical connection interface 16 allows the abutment 10 to be attached to a dental implant 18 (FIGS. 4a-4b), which dental implant 18 has an internal conical connection interface 20 corresponding to the conical connection interface 16 of the abutment 10/metal adapter 14. The metal adapter 14 may be coloured to match a colouring of the dental implant 18.

The conical connection interface 16 of the metal adapter 14 comprises an external conical shape 22 tapering towards the apical end 24 of the metal adapter 14. In other words, this portion of the metal adapter 14 has the external shape of a truncated cone. The conical connection interface 16 further comprises an external indexed portion 26. The indexed portion 26 is provided apically of the conical shape 22, proximal to the apical end 24 of the metal adapter 14. The indexed portion 26 may for instance be a hexagonal shape, which may have an externally hexagonal cross-section in a plane perpendicular to the longitudinal axis 28 of the abutment 10.

The metal adapter 14 further comprises a central recess 30 provided at the coronal end 32 of the metal adapter 14. The recess 30 is open towards the coronal end 32 of the metal adapter 14. The recess 30 comprises at least one, but preferably two opposite flat surfaces 34 that are parallel to the longitudinal axis 28. The recess 30 is surrounded by a circumferential load-bearing flat surface 38.

The ceramic part 12 further comprises a central protruding portion 40 (FIGS. 3a-3b) provided at the apical end 42 of the ceramic part 12. The protruding portion 40 has a circumferential side wall 44, with at least one but preferably two opposite flat surfaces 46 corresponding to the flat surface(s) 34 of the metal adapter 14. The protruding portion 40 is surrounded by a circumferential surface 48, which preferably is flat in a plane perpendicular to the longitudinal axis 28. The protruding portion 38 is generally adapted to be received in the recess 30 of the metal adapter 14.

The metal adapter 14 is removably attachable to the ceramic part 12. To this end, the metal adapter 14 may comprise at least one flexible arm 52 with a protrusion 50. The at least one flexible arm 52 may be arranged on a ledge 54 of the side wall 56 of the recess 30. The at least one arm 52 extends in a direction away from the apical end 24 of the metal adapter 14, and it is generally parallel to the longitudinal axis 28. The protrusion 50 is provided at the coronal free end of the flexible arm 52. The at least one protrusion 50 is inwardly directed. Inwardly here means substantially towards the central longitudinal axis 28 of the abutment 10. The at least one protrusion 50 may for instance project radially into the recess 30. The at least one protrusion 50 may have a limited extent in the axial direction. In other words, it has a defined height. The at least one protrusion 50 may be devoid of any right angles or undercuts, at least on its apical side.

The at least one arm 52 is flexible so that the free end with the protrusion 50 can move or flex radially (perpendicular to the longitudinal axis 28), as indicated by the arrow in FIG. 2a. The flexibility of the at least one arm 52 may be achieved and controlled by selecting suitable dimensions of the arm 52 given what material the adapter 14 is made of. The at least one protrusion 50 may be arranged apically of the coronal edge 53 of the at least one flat surface 34. Thereby the correct rotational relationship between the ceramic part 12 and the metal adapter 14 may be established before the ceramic part 12 reaches the protrusion(s) 50. In the illustrated embodiment, there are two arms 52 which are oppositely arranged in the circumferential direction.

Figures 3A, 3B:
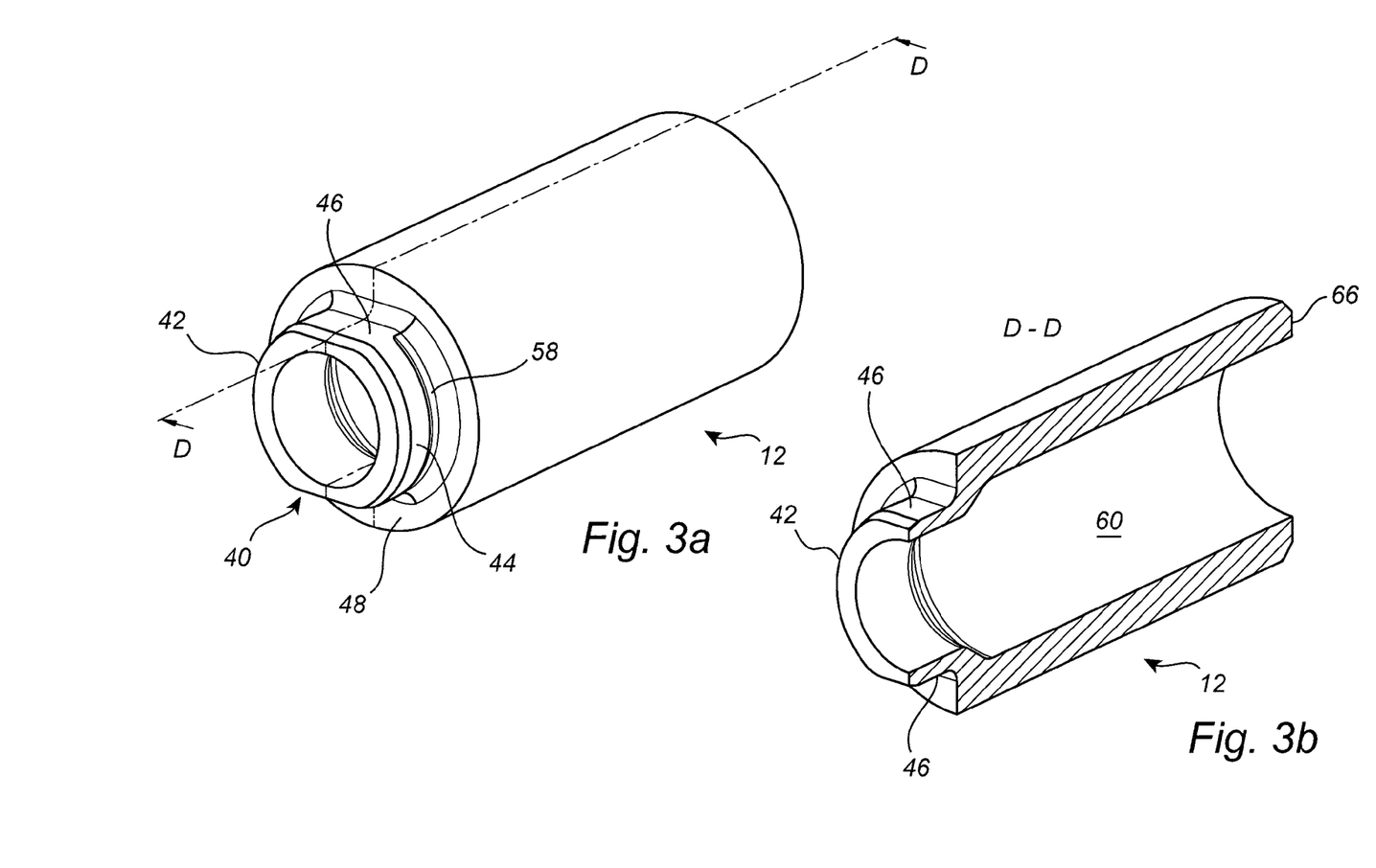

Further, the ceramic part 12 may optionally comprises at least one recess 58, which matches the at least one protrusion 50 of the metal adapter 14. In FIGS. 3a-3b, the ceramic part 12 has two outwardly open recesses 58 arranged on the protruding portion 40 at a distance from the apical end 42. Like the protrusions 50, the indentations 58 may have a limited height. Also like the protrusions 50, the indentations 58 may be curved or otherwise devoid of any right angles or undercuts, at least on their apical sides.

When the ceramic part 12 and the metal adapter 14 are mated, i.e. when the protruding portion 40 of the ceramic part 12 is received in the recess 30 of the metal adapter 14, the protrusions 50 press against the side wall 44 of the protruding portion 40, whereby the metal adapter 14 is attached axially (coronal-apical direction) to the ceramic part 12 by means of friction-fit. The protrusions 50 may be received in the recesses 58, whereby snap-locking may occur. However, the ceramic part 12 and the metal adapter 14 may again be separated if a sufficient axial force pulling them apart is applied. Hence, the metal adapter 14 is removably attachable to the ceramic part 12. With mainly elastic deformation of the two metal arms 52, the metal adapter 14 may be attached to and removed from the ceramic part 12 several times. The metal adapter 14 may be attached to (and removed from) the ceramic part 12 manually, without the use of tools or additional fastening means such as glue, screws, bolts, etc. Further, when the metal adapter 14 is attached to the ceramic part 12, the flat surfaces 46 of the ceramic part 12 abut against the flat surfaces 34 of the metal adapter 14, to prevent rotation of the metal adapter 14 relative to the ceramic part 12. Further, when the metal adapter 14 is attached to the ceramic part 12, the flat circumferential surface 48 of the ceramic part 12 abuts against the flat top surface 38 of the metal adapter 14. This allows for a load-bearing and a tight seal between the ceramic part 12 and the metal adapter 14.

The ceramic part 12 further comprises a screw channel 60. The screw channel 60 passes through the ceramic part 12, and forms a first opening 62a at a first end 64a of the screw channel 60 and a second opening 62b at a second (apical) end 64b of the screw channel 60. In this embodiment, the screw channel 60 is straight, with the first opening 62a at the coronal end 66 of the ceramic part 12 and the second opening 62b at the apical end 42 of the ceramic part 12. In the screw channel 60, there is provided a screw seat 68 proximal to the second end 64b. The screw channel 60 preferably includes an inclined surface defining said screw seat 68. The screw seat 68 is adapted to seat the head 70 of a screw 72 (FIG. 4b) used for fixing the abutment 10 to the dental implant 18. Opposite the head 70, the screw 72 has an external thread 74.

Instead of having a straight screw channel 60, the screw channel of the ceramic part can be angulated (not shown). That is, the longitudinal axis of the screw channel at the first end does not match the longitudinal axis of the screw channel at the second end 64b, whereby the first opening becomes situated at one of the sides of the ceramic part.

The metal adapter 14 further comprises a bore 76. The bore 76 passes through the metal adapter 14, and forms a coronal opening 78a and an apical opening 78b. When the ceramic part 12 and the metal adapter 14 are assembled, the screw channel 60 of the ceramic part 12 and the bore 76 of the metal adapter 14 are aligned. The bore 76 is provided with an internal thread 80. The internal thread 80 may be placed just apically of the recess 30. The internal thread 80 may facilitate recovery of the metal adapter from the dental implant 18. For example, by inserting the external thread of a retrieval tool (not shown) into the internal thread 80 of the metal adapter 14, and then pull away from the implant 18, the metal adapter 14 can be readily removed from the implant 18.

The dental implant 18 may for example be of the type disclosed in WO 2008/128757 A2, the content of which herein is incorporated by reference. However, other dental implants may be used as well, such as NobelReplace Conical Connection provided by Nobel Biocare. Among other things, the dental implant 18 comprises the internal conical connection interface 20. The internal conical connection interface 20 is open to the coronal end 82 of the dental implant 18, and comprises a conical chamber 84, a hexagonal interlock recess 86, and an internally threaded portion 88 (FIG. 4b).

When the abutment 10 is attached to the dental implant 18, the metal adapter 14 of the abutment 10 is partly inserted into the internal conical connection interface 20 of the implant 18. The conical shape 22 of the metal adapter 14 abuts against the conical chamber 84, whereas the indexed portion 26 interlocks with the hexagonal interlock recess 86 to prevent rotation. The screw 72 is then inserted. The screw 72 extends through the screw channel 60 and the bore 76, and further into the internally threaded portion 88, where the external thread 74 of the screw 72 engages said threaded portion 88. By turning the screw 72 with a suitable tool (not shown), the screw head 70 is pressed against the screw seat 68 in the ceramic part 12, and the abutment 10 may be fixed to the implant 18. Also, the metal adapter 14 is clamped between the ceramic portion 12 and the dental implant 18. Overall, an adapter 10 is provided which has a high strength, non-brittle material in the implant connection (i.e. the metal adapter 14) in combination with high esthetic ceramics (the ceramic part 12). Also, the fact that the metal adapter 14 may be detached from the ceramic part 12 enables fusing of porcelain to the ceramic part 12 without having to heat the metal adapter 14.

Figure 4A:
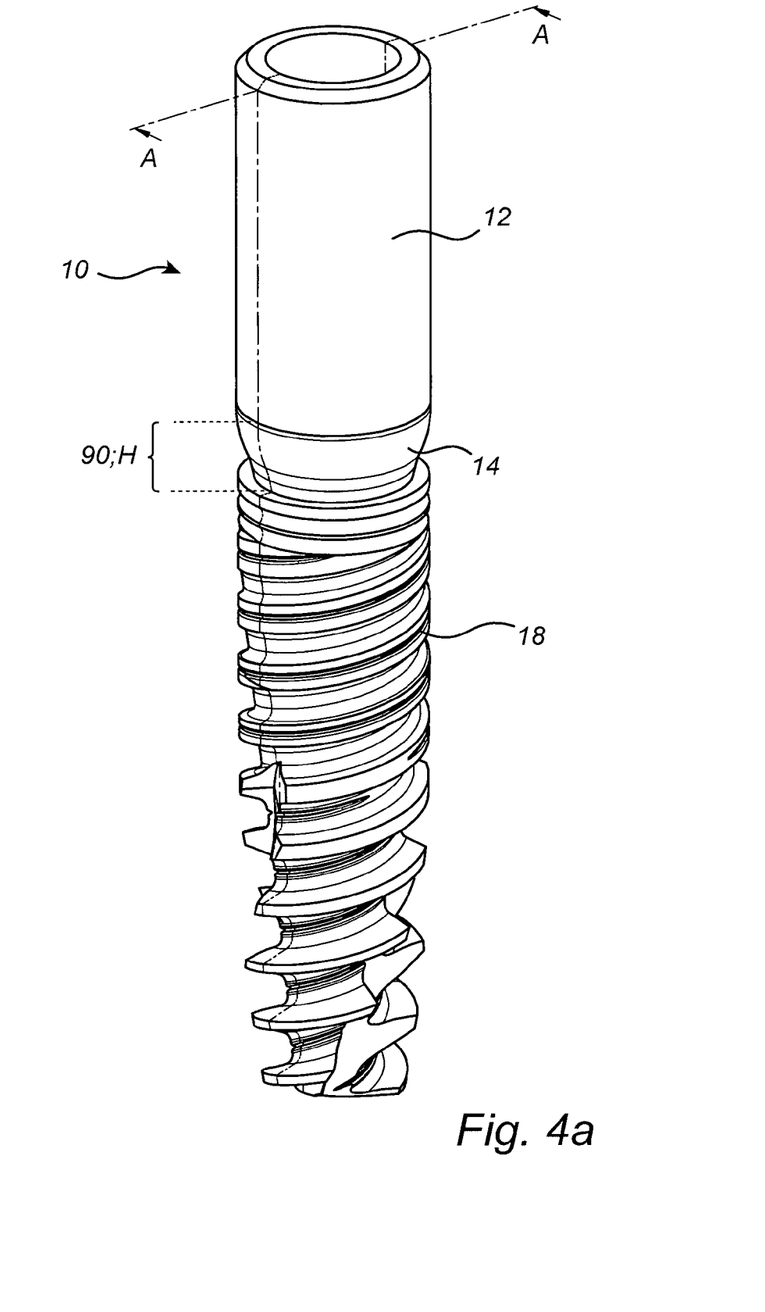
FIG. 4a is a perspective view of the abutment of FIGS. 1a-1b fixed to a dental implant.
Figure 4B:
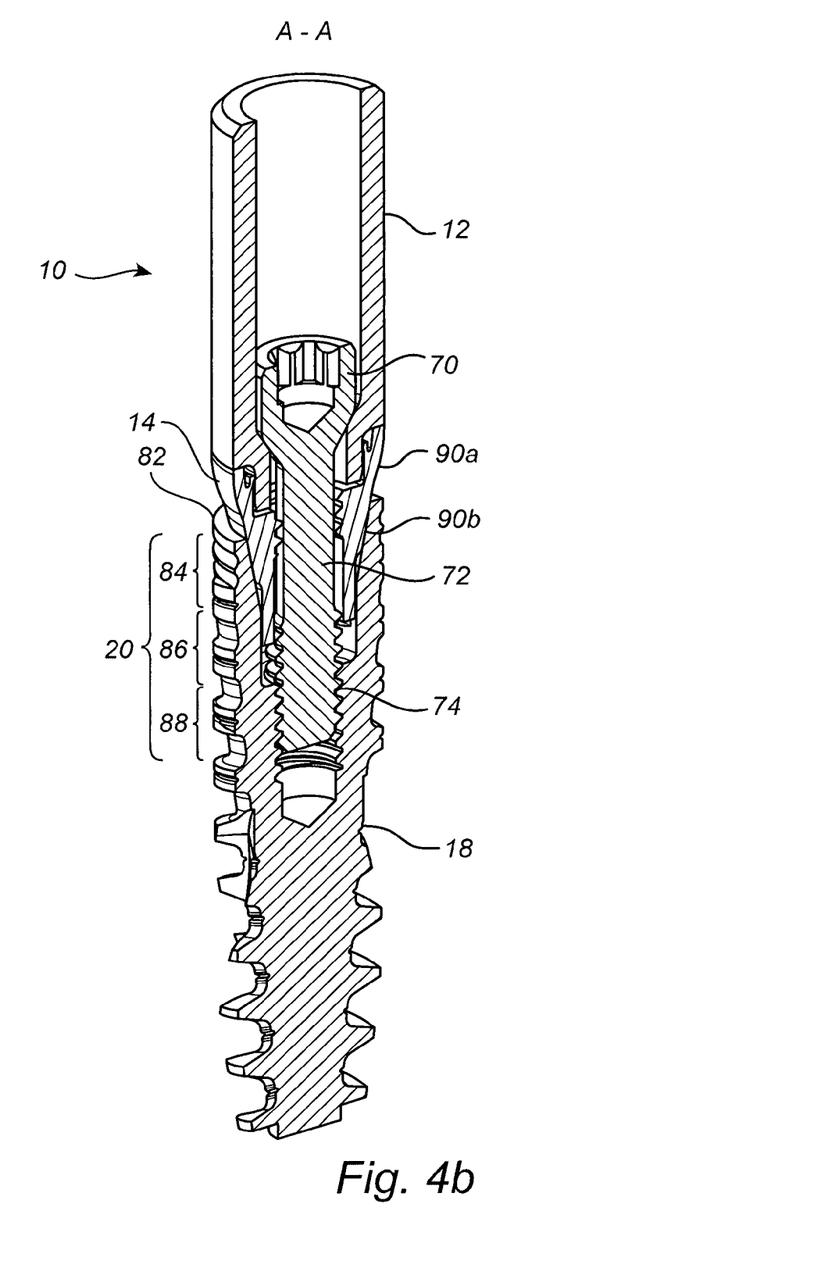

As the abutment 10 is fixed to the dental implant 18, an outer surface 90 of the metal adapter 14 between the ceramic part 12 and the dental implant 18 remains exposed to the outside, as seen in FIGS. 4a-4b. The outer surface 90 is preferably devised for soft tissue apposition. That is, the outer surface 90 is supposed to face the gum of the patient. The surface 90 may have a height H of about 1.5 mm. Also, the surface 90 may be coloured to resemble the gingival (soft tissue).

Also when the abutment 10 is fixed to the dental implant 18, there is no point of contact between the ceramic part 12 and the dental implant 18, cf. the metal adapter of WO2004002358. Also, since the ceramic part 12 has the apically protruding portion 40 received in the coronal recess 30 of the metal adapter 14, the screw seat 68 and screw head 70 may be situated relatively close to the implant 18, cf. the embodiments of FIGS. 5a-5b and 6a-6b.

The dental implant to which the abutment 10 is attached may be anchored in the jaw bone of a patient, or it may be arranged in a physical model. In the latter case, the dental implant may be a replica or implant analog.

A suitable way of attaching the abutment 10 to the dental implant 18 is described in Applicant's co-pending application entitled "METHOD OF ATTACHING A DENTAL COMPONENT TO A DENTAL IMPLANT", the content of which herein is incorporated by reference.

Figure 5A:
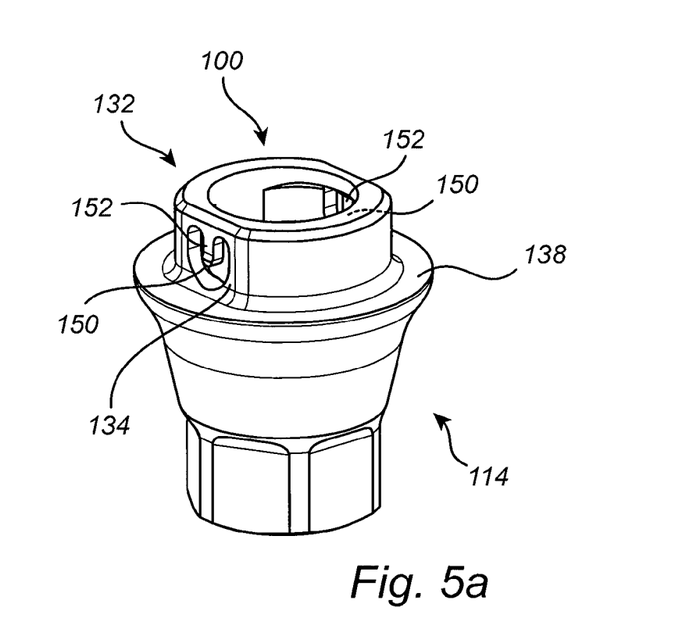
FIGS. 5a-5b are perspective views of a metal adapter and ceramic part according to another embodiment of the present invention.
Figure 5B:
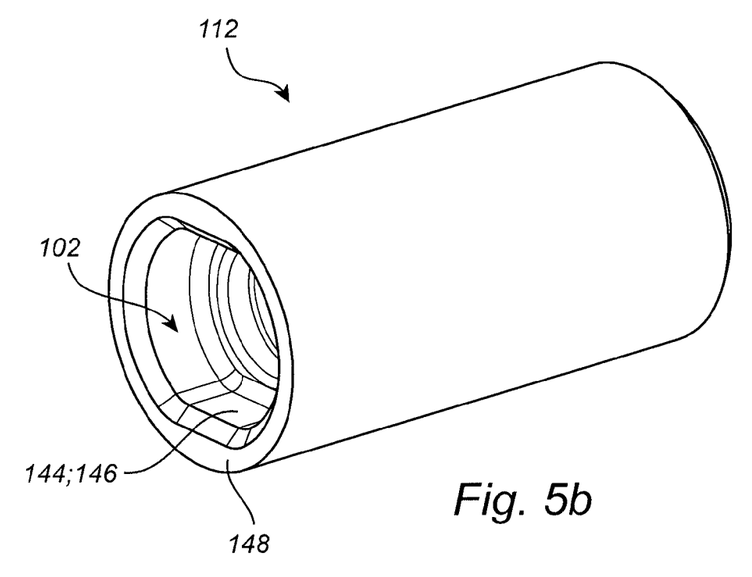
Figure 6A:
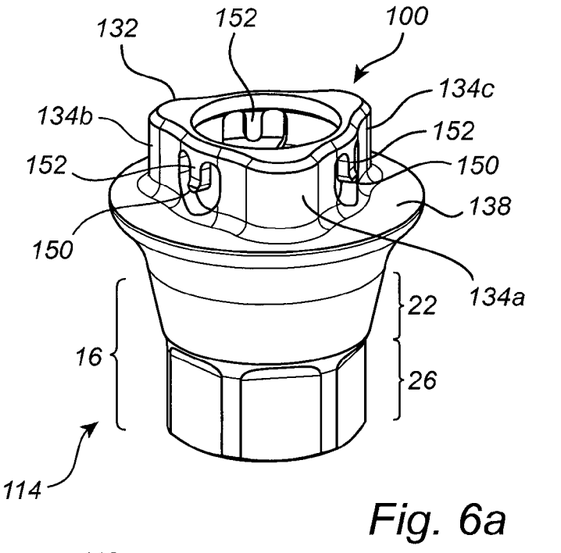
FIGS. 6a-6b are perspective views of a metal adapter and ceramic part according to yet another embodiment of the present invention.
Figure 6B:
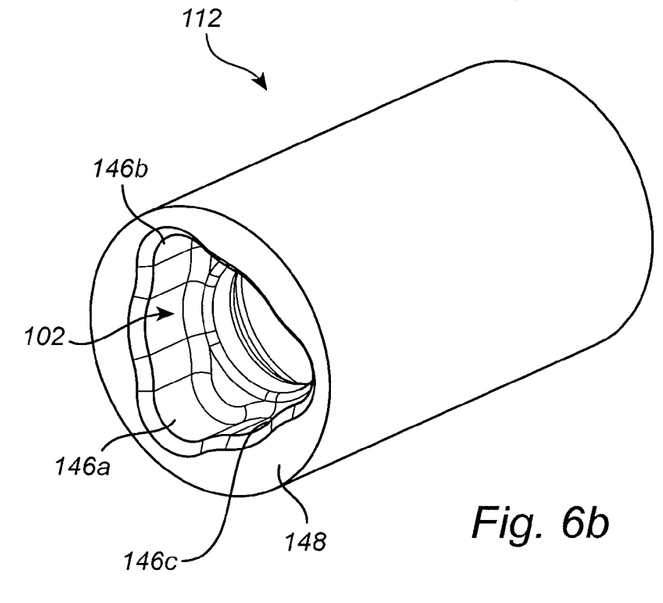
Figure 6C:
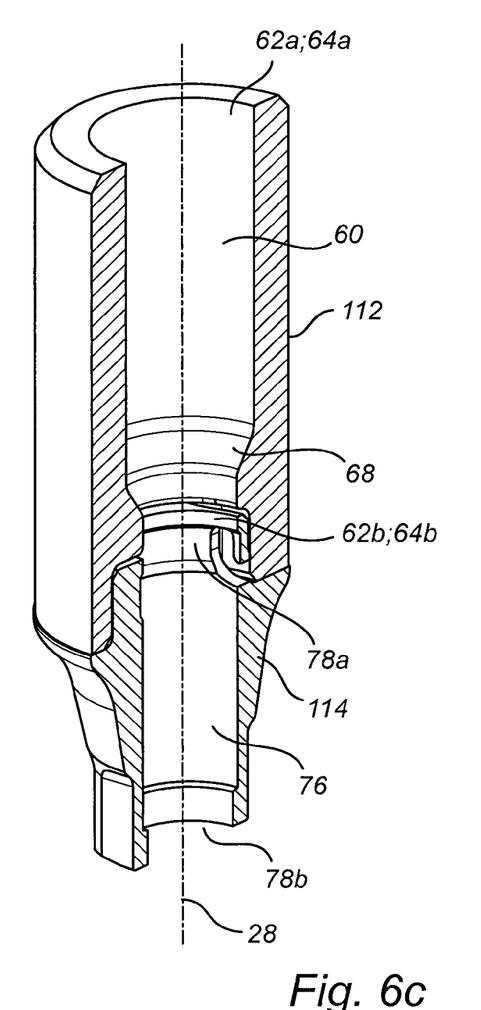
FIG. 6c is a cross-sectional view of the metal adapter of FIG. 6a attached to the ceramic part of FIG. 6b.
Figure 6D:
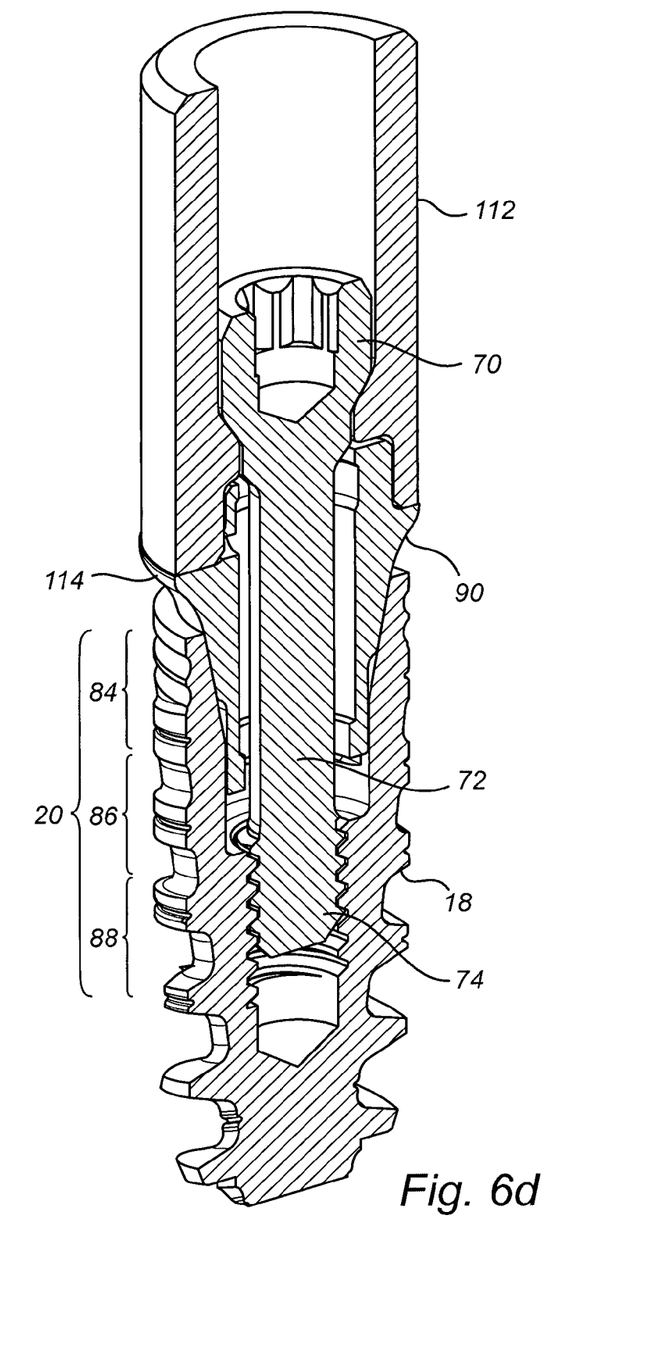
FIG. 6d is a cross-sectional view of the metal adapter of FIG. 6a and the ceramic part of FIG. 6b attached to a dental implant.

FIGS. 5a-5b show a metal adapter 114 and ceramic part 112 according to another embodiment of the present invention. The metal adapter 114 and ceramic part 112 in FIGS. 5a-5b may be similar to the metal adapter 14 and ceramic part 12 shown in FIGS. 1-4, but differ when it comes to the interface between them. The metal adapter 114 has at its coronal end 132 a central protruding portion 100. The protruding portion 100 is adapted to be received in a central apical recess 102 of the ceramic part 112. The protruding portion 100 is surrounded by a circumferential load-bearing ledge 138. The protruding portion 100 comprises two opposite flexible arms 152, each with an outwardly directed protrusion 150. The protrusion 150 is arranged at the free apical end of the respective arm 152. The ceramic part 112 may optionally comprise at least one inwardly open recess matching the two protrusions 150 and arranged in a side wall 144 of the central apical recess 102. When the metal adapter 114 is attached to the ceramic part 112, the two protrusions 150 are pressed against the side wall 144 for securing the metal adapter 114 to the ceramic part 112. Also, the circumferential ledge 138 may abut against a corresponding circumferential rim 148 of the ceramic part 112. Two opposite flat surfaces 134 on the protruding portion 100 of the metal adapter 114 may match with corresponding flat surfaces 146 in the central apical recess 102 of the ceramic part 112 to serve as a rotation lock. Alternatively, the surfaces on the protruding portion of the metal adapter 114 may be convex 134a-c, and the matching surfaces of the ceramic part 112 may be concave 146a-c, as seen in the embodiment shown in FIGS. 6a-6d. In FIGS. 6a-6d, there are three convex surfaces 134a-c uniformly distributed in the circumferential direction on the metal adapter 114, and three concave surfaces 146a-c uniformly distributed in the circumferential direction in ceramic part 112. Likewise on the metal adapter 114, there are three flexible arms/protrusions arranged between the three convex surfaces 134a-c.

The person skilled in the art realizes that the present invention by no means is limited to the preferred embodiments described above. On the contrary, many modifications and variations are possible within the scope of the appended claims.

For example, instead of friction-fit and/or snap-locking, the metal adapter may be removably attached to the ceramic part by other connection means, such as form-fit, force-fit, press-fit, finger spring, ring friction, point contact deformation, bayonet connection, friction ridges, surface roughness, etc.

The invention claimed is:

1. An abutment, comprising:
a ceramic part; and
a metal adapter removably attachable to the ceramic part,
wherein the metal adapter has a conical connection interface adapted to attach to a dental implant,
wherein the metal adapter comprises at least one flexible arm with a protrusion adapted to press against a side wall or snap into any corresponding recess of the ceramic part to secure the metal adapter to the ceramic part in the coronal-apical direction,
wherein the metal adapter comprises at least one convex surface adapted to abut against at least one corresponding concave surface of the ceramic part to prevent rotation between the ceramic part and the metal adapter,
wherein the metal adapter at its coronal end has a central protruding portion which is adapted to be received in a central apical recess of the ceramic part, and
wherein said central protruding portion accommodates said at least one convex surface and said at least one flexible arm is housed within said central protruding portion.

2. The abutment according to claim 1, wherein said at least one convex surface is three convex surfaces uniformly distributed in the circumferential direction on the metal adapter, wherein said at least one corresponding concave surface is three concave surfaces uniformly distributed in the circumferential direction in the ceramic part, and wherein the metal adapter comprises three flexible arms and protrusions arranged between the three convex surfaces.

3. The abutment according to claim 1, wherein the metal adapter includes a load-bearing circumferential surface adapted to abut against a corresponding circumferential surface of the ceramic part.

4. The abutment according to claim 1, wherein the conical connection interface of the metal adapter includes an external conical shape tapering towards the apical end of the metal adapter and adapted to mate with a corresponding conical surface of the dental implant, and an external indexed portion provided apically of the conical shape adjacent to the apical end of the metal adapter.

5. The abutment according to claim 1, wherein the metal adapter includes an outer surface adapted to appose soft tissue.

6. The abutment according to claim 3,
wherein the conical connection interface of the metal adapter includes an external conical shape tapering towards the apical end of the metal adapter and adapted to mate with a corresponding conical surface of the dental implant, and an external indexed portion provided apically of the conical shape adjacent to the apical end of the metal adapter,
wherein the metal adapter includes an outer surface adapted to appose soft tissue, and
wherein said outer surface is arranged between said load-bearing circumferential surface and said external conical shape.

7. The abutment according to claim 1, wherein the ceramic part comprises a screw channel passing through the ceramic part and forming a first opening at a first end and a second opening at an apical end, and a screw seat proximal to the apical end of the screw channel to seat the head of a screw for the fixation of the abutment to the dental implant.

8. The abutment according to claim 7, wherein the longitudinal axis of the screw channel at the first end does not match the longitudinal axis of the screw channel at the apical end.

9. The abutment according to claim 1, wherein the metal adapter comprises a bore passing through the metal adapter and forming a coronal opening and an apical opening, and wherein the bore is provided with an internal thread.

10. The abutment according to claim 1, wherein the ceramic part is adapted to support a dental restoration.

11. The abutment according to claim 1, wherein the ceramic part is a full-contour part.

12. The abutment according to claim 1, in combination with the dental implant.

13. The abutment according to claim 1, wherein the protrusion is adapted to press against the side wall and snap into any corresponding recess of the ceramic part.

14. A method of attaching the abutment of claim 5 to a dental implant anchored in a jaw bone of a patient, wherein the coronal end of the dental implant is substantially in level with the surface or crest of the jaw bone, the method comprising:
attaching the abutment to the dental implant, such that said outer surface of the metal adapter is exposed to soft tissue or gum overlying the jaw bone.

* * * * *